(12) United States Patent
Khayat

(10) Patent No.: US 8,097,773 B2
(45) Date of Patent: Jan. 17, 2012

(54) PROCESS FOR SELECTING BANANA CLONES AND BANANA CLONES OBTAINED THEREBY

(75) Inventor: Eliahu Khayat, Neve Ziv (IL)

(73) Assignee: Rahan Meristem (1998) Ltd, Kibbutz Rosh Hanikra (IL)

( * ) Notice: Subject to any disclaimer, the term of this patent is extended or adjusted under 35 U.S.C. 154(b) by 734 days.

(21) Appl. No.: 12/042,177

(22) Filed: Mar. 4, 2008

(65) Prior Publication Data

US 2008/0229443 A1    Sep. 18, 2008

Related U.S. Application Data

(63) Continuation of application No. 11/021,937, filed on Dec. 23, 2004, now abandoned.

(51) Int. Cl.
*A01H 5/00* (2006.01)
(52) U.S. Cl. ........................................ 800/298
(58) Field of Classification Search .................. None
See application file for complete search history.

(56) References Cited

U.S. PATENT DOCUMENTS

PP8,983 P      11/1994   Rowe
2004/0096875 A1 *  5/2004   Hirochika et al. ............ 435/6

OTHER PUBLICATIONS

Khayat et al. Banana improvement program at Rahan Meristem. (1998) Acta Hort.; vol. 490; pp. 71-78.*
Khayat et al. Proposed mechanism for the occurrence of the "long narrow leaf" (LNL) "Cavendish" mutant in micropropatated "Cavendish" bananas. (1999) INFOMUSA; vol. 8; pp. 1-16.*
Hirochika, Hirohiko et al.; "Retrotransposon families in rice"; 1992, *Moi Gen Genet*, vol. 233, pp. 209-216.
Hirochika, Hirohiko et al.; "Retrotransposons of rice involved in mutations induced by tissue culture"; 1996, *PNAS*, vol. 93, pp. 7783-7788.
Jain, S. Mohan; "Tissue culture-derived variation in crop improvement"; 2001, *Euphytica*, vol. 118, pp. 153-166.
Khayat, E. et al.; "Banana improvement program at Rahan Meristem"; 1998, *ACTA Hort.*, vol. 490, pp. 71-78.
Khayat, E. et al.; "Proposed mechanism for the occurence of the <<long narrow leaf>> (LNL) "Cavendish" mutant in micropropagated "Cavendish" bananas"; 1999 *INFOMUSA*, vol. 8, No. 2, pp. 1-16.
Khayat, E. et al.; "Banana Improvement: Cellular, Molecular Biology, and Induced Mutations; Chapter 9: Somaclonal variation in Banana (*Musa acuminate* cv. Grande Naine). Genetic mechanism, frequency, and application as a tool for clonal selection"; 2004, *Science*, pp. 97-109.
"PRO*MUSA* Fusarium wilt working group meeting"; 1999, *INFOMUSA*, vol. 8, No. 2, pp. 1-16.
Walther et al.; Proceedings of the 3rd International ISHS Symposium on In Vitro Culture and Horticulture Breeding; 1996, pp. 379.383.

* cited by examiner

*Primary Examiner* — Cathy Kingdon Worley
(74) *Attorney, Agent, or Firm* — Lyn R Marantz; KK Patents, LLC

(57) ABSTRACT

The invention provides a process for selecting banana clones that are characterized by increased bunch weight and by increased total fruit yield, which process is based on somaclonal variation and comprises the steps of initiating tissue cultures from apical meristem explants, and propagating and rooting the same; hardening, potting, and growing in vivo, plants propagated in the previous step; forming a mat from a cluster of plants grown in the previous step originating from the same clone; planting the mats from the previous step in a field, and growing them under conditions of abiotic stress, the conditions including the growth of the mats in an area wherein the average winter night temperature is below 10° C.; measuring bunch weight and total fruit yield of the mats for a period of at least 3 years and selecting mats, the plants of which exhibit the best characteristics of increased bunch weight and increased total fruit yield; and utilizing mats selected in the previous step for preparing apical meristem explants.

2 Claims, 8 Drawing Sheets

Average bunch weight
Comparison between Rahan and Local clones in the Philippines 'BOX / STEM' RATIO
Comparison between Rahan and Local clones in the Philippines PCR (panel A) and RT-PCR (panel B) products using TOS 17 primers
to amplify Ban-Retro 1. Lanes 1-5 in panel A represent PCR products from
DNA samples of plantlets at different duration periods in tissue culture.
Lanes 7-12 in panel B represent different RNA samples used for RT-PCR
with (+) or without (-) RT enzyme (control). Lane 6 – molecular marker DNA
(*Hind* III cut Phi-X).

Southern hybridization of control (lanes 5,6) and LNL mutants (lanes 1-4) genomic DNA with $^{32}$P labeled Ban-Retro 1 probe. Ten µg DNA were either uncut with EcoR 1(lanes 2,4,6) or cut (lanes 1,3,5).

PROCESS FOR SELECTING BANANA CLONES AND BANANA CLONES OBTAINED THEREBY

CROSS-REFERENCES TO RELATED APPLICATIONS

This application is a continuation of application Ser. No. 11/021,937 filed Dec. 23, 2004, entitled "A PROCESS FOR SELECTING BANANA CLONES AND BANANA CLONES OBTAINED THEREBY", now abandoned; which disclosure is incorporated herein by reference for all purposes.

FIELD OF THE INVENTION

The present invention relates to a process for selecting superior banana clones which is based on somaclonal variation and comprises tissue culture propagation of apical meristems, hardening, and growing the plants under stressful climate conditions for selection of superior clones.

BACKGROUND OF THE INVENTION

Plant tissue culture even when started from a single cell can express variations particularly after repeated subcultures, suggesting an emergence of variability; this variation is called somaclonal variation. Somaclonal variation, is not fully understood and possibly comprises chromosome alterations, gene amplification, point mutations, or DNA methylation, may cause changes in crop species ("off-types"), but can also be utilized for selecting useful variants [Larkin P. J. et al.: Theor. Appl. Genet. 60 (1981) 197-214] providing an alternative to the methods of improving agricultural crops by hybridizations or genetic manipulations. Somaclonal variation may, on one hand, enable germplasm improvement without the numerous crossings used in traditional breeding methods, and on the other hand it is not subjected to the public's concern as in cases of genetically modified organisms.

Banana, with an approximate world production of 100 million tons per year, is an important crop plant, although cultivation in tropical regions is complicated by an assortment of parasites comprising viruses, fungi, and nematodes. Since most cultivated varieties of banana are sterile, banana breeding is a slow, complex, and expensive process. Cultivated bananas are natural selections originating from the center of origin of the genus *Musa* in the Asian Pacific region. The edible types comprise a range of natural hybrids originating from the two species *Musa Acuminata* (A genome) and *Musa Balbisiana* (B genome). Most cultivars are triploids (AAA, AAB, or ABB genomes), parthenocarpic and sterile, though in the international trade of dessert bananas, the vast majority belong to the AAA 'Cavendish' subgroup. The main focus of banana breeding programs is resistance to diseases and improvements of fruit quality. The extreme susceptibility of the old cultivars to *Fusarium wilt* (Panama Disease) forced the producers to shift to more resistant varieties. The purpose of this invention is to provide a novel process for selecting banana clones, based on somaclonal variation.

Attempts to utilize somaclonal variation for improving agriculture plants bring usually only modest success, partially due to a very limited control over said variations and due to incomplete knowledge of the mechanisms involved in them, and partially due to niceties of the necessary tissue culture techniques. The exact conditions required to initiate and sustain plant cells in culture, or to regenerate the plant from cultured cells, are very unique for each species and even for each variety. Further, the identification and selection of the improved clones may be quite complex, the differences being evident only at certain stages of clone development [see, e.g., Walther R. et al.: Acta Hort. 447 (1997) 379-86].

Since there is a continuing need of new banana clones, expressing higher yield and better quality of the fruit, it is the objective of this invention to provide a technique—based on somaclonal variation—for selecting banana clones which are characterized by increased bunch weight and fruit yield.

Other objectives and advantages of present invention will appear as description proceeds.

BRIEF SUMMARY OF THE INVENTION

The present invention provides a process for selecting banana clones that are characterized by increased bunch weight and by increased total fruit yield. The selection is mediated by somaclonal variation and comprises the steps of initiating tissue cultures from apical meristem explants; their propagation and rooting; hardening; potting; planting the mats from the previous step in the field; growing them under conditions of abiotic stress conditions prevailing in the Western Galilee in Israel or other stressful environments, comprising the average winter night temperature below 10° C.; evaluating the mats over a sufficient period comprising measuring bunch weight and total fruit yield; utilizing the mats selected in the previous step for propagating apical meristem explants of the subsequent step; and subsequent to the propagation of a selected clone, putting the plant in the field and re-evaluating it for trueness to type. Said abiotic stress may further comprise at least one stress factor selected from the group consisting of the minimal winter night temperature being below 10° C., the average rainfalls during three summer months being lower than 200 mm, and the average summer day temperature being higher than 28° C. Preferably, a process according to this invention comprises even more stress factors. A sufficient period for said evaluation of mats is a period comprising at least three fruit cycles.

The invention further relates to generation of novel banana clones, and to the selected clones themselves, preferably comprising either Jaffa or Gal clones.

More particularly according to the present invention there is now provided a process for selecting banana clones that are characterized by increased bunch weight and by increased total fruit yield, which process is based on somaclonal variation and comprises the steps of:
  a) initiating tissue cultures from apical meristem explants, and propagating and rooting the same;
  b) hardening, potting, and growing in vivo, plants propagated in step a;
  c) forming a mat from a cluster of plans grown in step b, originating from the same clone;
  d) planting the mats from the previous step in a field, and growing them under conditions of abiotic stress, said conditions including the growth of said mats in an area wherein the average winter night temperature is below 10° C.;
  e) measuring bunch weight and total fruit yield of said mats for a period of at least 3 years and selecting mats, the plants of which exhibit the best characteristics of increased bunch weight and increased total fruit yield; and
  f) utilizing mats selected in the previous step for preparing apical meristem explants.

In preferred embodiments of the present invention, said process comprises the further steps of:

g) initiating tissue cultures from apical meristem explants, from step f, and propagating and rooting the same;

h) hardening, potting, and growing in vivo, plants propagated in step g;

i) forming a mat from a cluster of plants grown in step h, originating from the same clone;

j) planting the mats from the previous step in a field, and growing them under conditions of abiotic stress, said conditions including the growth of said mats in an area wherein the average winter night temperature is below 10° C.;

k) measuring bunch weight and total fruit yield of said mats for a further period of at least 1 year in order to re-evaluate for trueness of type and selecting mats, the plants of which exhibit the best characteristics of increased bunch weight and increased total fruit yield.

Preferably said stress conditions comprise at least one further stress item selected from the group consisting of maintaining the mats in an area receiving average rainfalls during three summer months lower than 200 mm, and subject to an average summer day temperature higher than 28° C.

In another aspect of the present invention there is provided a banana clone obtained in a process as defined above.

In especially preferred embodiments of the present invention, there is provided a banana clone obtained in a process as defined above, wherein said banana clone is designated as a Jaffa or Gal clone, said clone having the characteristics as set forth in tables 2B and 3B hereinafter.

While the invention will now be described in connection with certain preferred embodiments in the following examples and with reference to the accompanying figures so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

BRIEF DESCRIPTION OF THE DRAWINGS

The above and other characteristics and advantages of the invention will be more readily apparent through the following examples, and with reference to the appended drawings, wherein.

DETAILED DESCRIPTION OF THE INVENTION

Figure 1A:
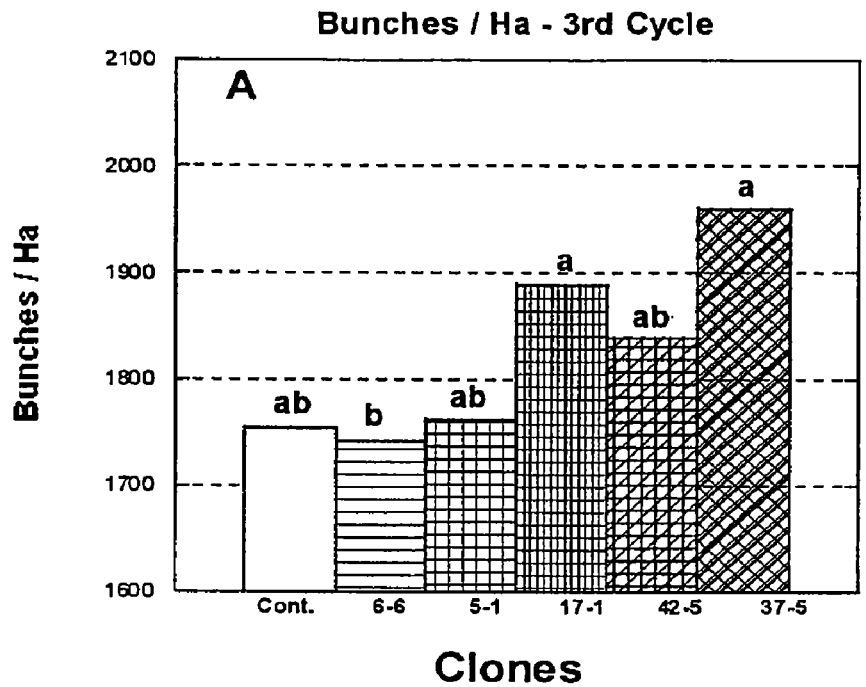
FIGS. 1A and 1B are graphs showing the number of bunches per hectare for selected clones.

It now has been surprisingly found that growing mats that have been obtained from tissue cultures initiated from apical meristem, under conditions of abiotic stress characteristic of the Western Galilee (Israel), situated on the border line of commercial banana production, can yield superior banana clones characterized by increased bunch weight, increased total fruit yield, and as well as by increased resistance.

Introduction of in vitro culturing allowed production of pathogen free banana plants and widened the genetic variability of existing cultivars, as a result of somaclonal variation [Walther R. et al.: Acta Hort. 447 (1997) 379-86]. An example of a banana cultivar improved by somaclonal variation was demonstrated by Hwang [e.g., Hwang S. C. et al.: Acta Horticulturae 275 (1990) 417-23] who selected somaclones resistant to *F. oxysporum*.

In the present invention banana plants were grown under harsh climate stress conditions. The Western Galilee in Northern Israel is on the border line of commercial banana production. In the summer months solar radiation reaches very high levels, ambient temperatures are high and rainfall is practically nil. During winter nights temperatures occasionally drop below the freezing point, severely damaging banana plants. Another unique factor of this selection process is that it utilizes the conditions of an area in which no endemic banana disease-causing organisms exist, and the plants are renewed every spring, not carrying the load of the previous growing cycles. The selection was performed on a 30 Ha area, selecting the best 5% of the field and bringing to the lab the selected clones. The conventional TC procedure was used. Every year, approximately 20% of the plants were replaced on said 30 Ha area.

Sucker selection was practiced during the summer months and was aimed at restricting flowering to mid summer of the next year and harvesting to the following winter months. Sucker selection was based on the number of accumulated leaves on specific dates. The "selector" determines the number of suckers to be left for the next cycle in each mat according to physiological conditions of the plants in the specific mat and how it compares to adjoining mats. Yield is determined mainly by the number of bunches/mat (usually 1-3 per mat) and the weight of each bunch. In tropical regions like the Philippines, the number of bunches per mat is fixed (usually only one). Therefore the clonal evaluation comprises bunch weight only. Due to the relatively "harsh" climatic conditions and unique topographic location combined with strict quarantine measures, the Western Galilee is free of the major banana pests and diseases, including Black and Yellow Sigatoka, Banana Bunchy Top Virus, Banana Streak Virus, Panama disease and the most damaging nematode *Radopholus similis*. The vectors that transmit these diseases seem unable to overcome either the cold winter temperatures or the low humidity in the long and dry summers.

Components of yield in bananas include the number of bunches per mat, the weight of each bunch and the number of mats per hectare, which together determine the potential production in tons per hectare. Another important factor worth considering (mainly for exporting producers) is fruit quality, with emphasis on finger size and appearance of the fruit. Since yield had a positive correlation with all the parameters used in our initial selection, we predicted that the selection process for total yield, used in Israel, would be useful in the tropics as well. Although a narrow genetic base was sampled in our initial selection program, the quantitative and qualitative parameters were manifested in the subsequent field trials. The clones selected performed above the mean values measured for the total population in all the relevant parameters, such as the number of bunches per mat, average bunch weight and total yields per hectare.

The second step of clonal evaluation was performed on more than 120 bunch-bearing plants per year, of each of the selected clones. The achievements of these clones in total yield, though differing from each other, were consistently above the control population.

It is likely that a mixed population of several selected clones will be advantageous in a different ecological environment. Furthermore, to avoid deleterious effects due to a mono-culture population, we combined all five clones for evaluation in the Philippines. Propagation by meristem culture allowed an even mix of the clonal selections.

Figure 4:
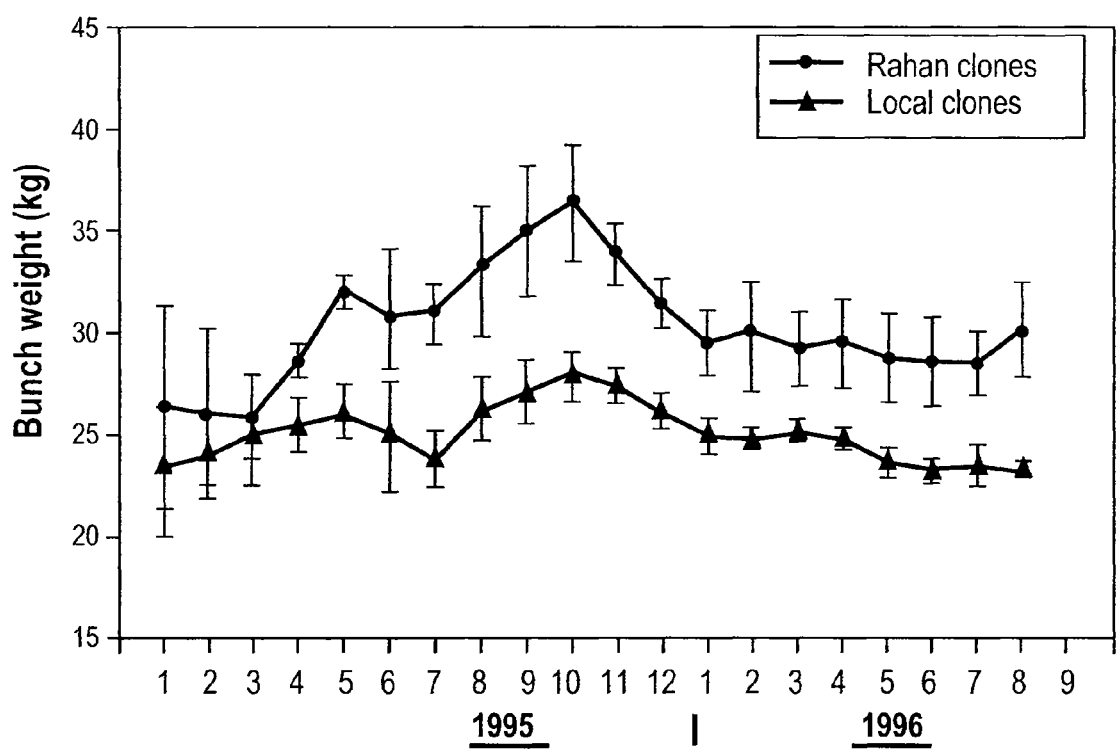
FIG. 4 is a graph comparing bunch weights of "R" selection and "L" selection.
Figure 5:
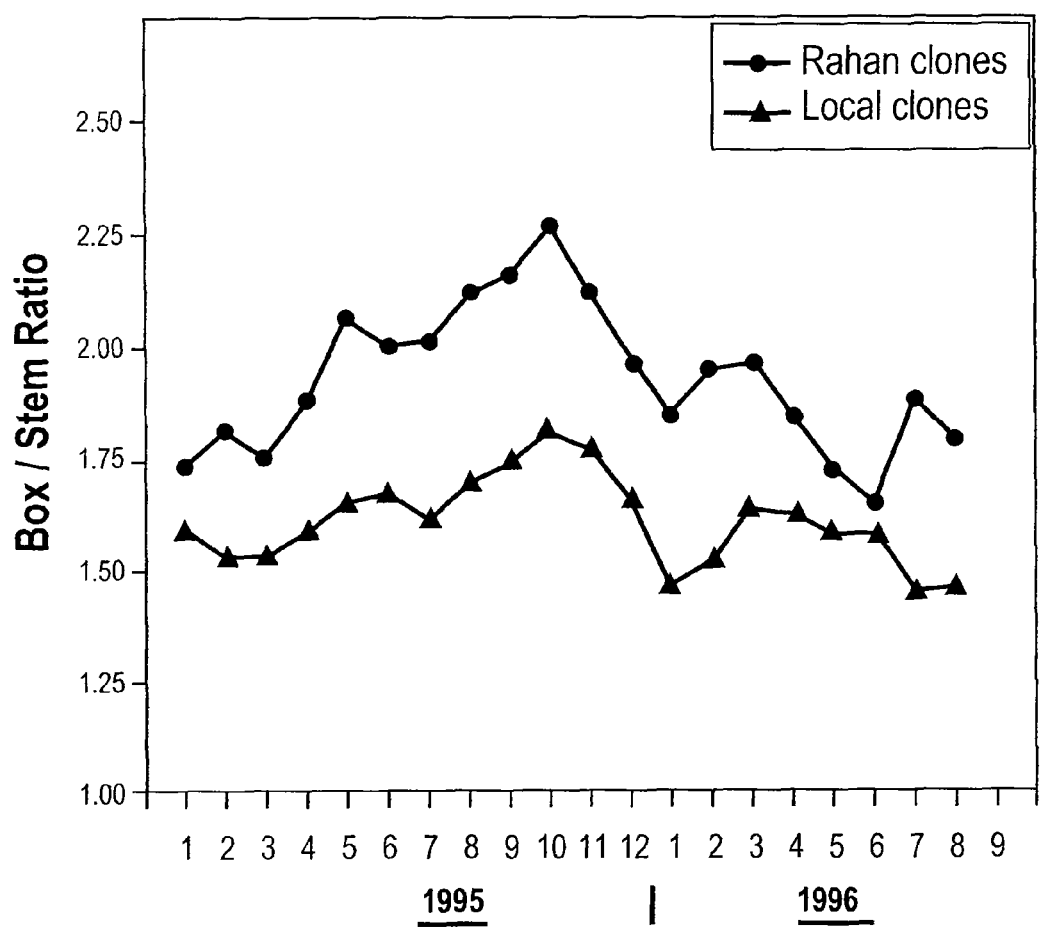
FIG. 5 is a graph comparing box/stem ratio of "R" selection and "L" selection.
Figure 6:
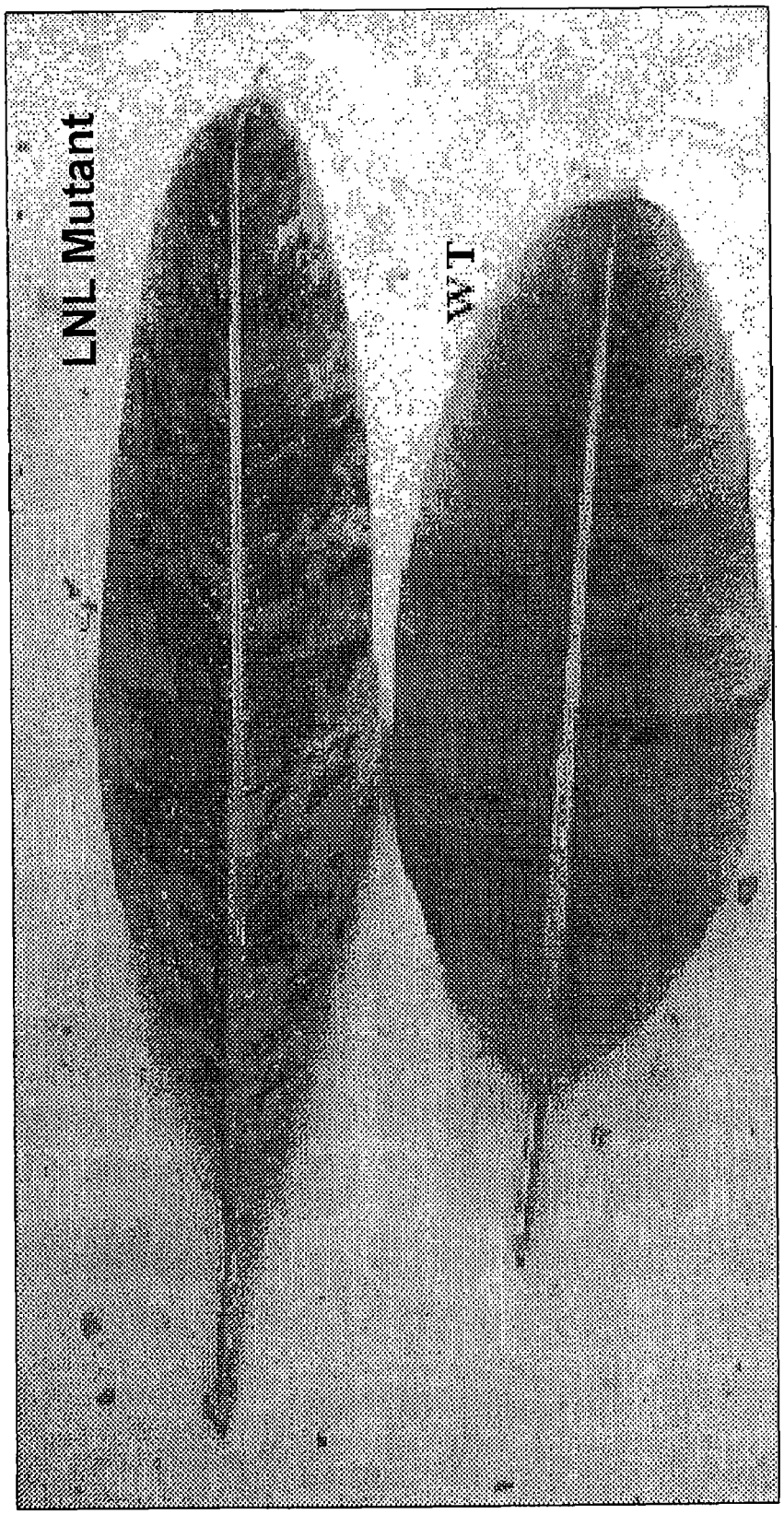
FIG. 6 is a photo of leaves corresponding to two clones, Long and Narrow Leaf (LNL) mutant, and Wild Type (WT)

Another crucial parameter for the banana export industry is fruit quality. Fruit loss due to inferior quality can reach 40 percent in some cases. To include this important characteristic in our evaluation, the yield for the Philippines was expressed as "box/stem ratio" in addition to "bunch weight" (rather than fruit yield per hectare). This ratio was significantly higher for the clones selected in The Western Galilee of Israel compared to clones selected locally in the Phillippines (FIG. 5). The difference reached an average value of 18 percent for the entire evaluation period and peaked during the most productive period around October 1995. Similar results were achieved with bunch weight values (FIG. 4). The fact that each of the clones (the one selected in the Philippines and the one selected in Israel) clearly differed in various components of yield, shows that selection is influenced by environmental conditions. The geographic location of the Western Galilee allows selection unmasked by the effects of diseases and pests.

The data, presented herein, indicate that selection in the ecological conditions of the Western Galilee provides better results in ecosystems that involve biotic pressures.

The limited gene pool of cultivated bananas for the export industry has led researchers to use alternative methods of germplasm improvement such as mutation breeding [Novak F. J. et al.: Tropical Agriculture (Trinidad) 67(1) (1990) 21-8] and recombinant DNA technology [May G. D. et al.: Biotechnology 13 (1995) 486-92]. However, since both of these techniques rely on small genetic changes, normally single genes, it is crucial to start with a good genetic baseline and with plants free of viruses. In this regard, our data suggest that pre-selected clones in marginal climates for banana production are advantageous.

Clonal selection of banana (*Musa acuminata* AAA, cv. 'Grande Naine') was performed under the marginal climatic conditions for banana cultivation as mentioned above. The initial selection was carried out on 300 mats originating from six mother clones multiplied by the meristem culture. Five clones were selected for further experiments. In the third growth cycle the total number of bunches per hectare of three out of the five selections, exceeded that of the control, while the remaining two selections performed similar or below the control. In the fourth cycle all the selections out-performed the control. Average bunch weights of two of the selected clones were significantly higher than the control. The total yield, derived from bunch weight and the number of bunches per mat of each of the selections, was higher than that of the control in both the third and the fourth cycle. One hundred and fifty hectares of micropropagated plants derived from the selected clones were planted in the Philippines, and their performance was evaluated and compared to that of a local selection of 'Grande Naine'. The yield of the Israeli selected clones in the Philippines was significantly higher by an average value of 18 percent compared to the local clones.

Using degenerate primers, a fragment of a retro-transposable element (BR-1) that was induced by extensive in vitro culture was detected in Musa. Transcriptional activation of the banana retro-transposon was detectable by RT-PCR in the 'Long and Narrow Leaf' mutant (LNL). The frequency of occurrence of BR-1 was analyzed in genomic DNA of the LNL mutant and in its originator non-mutant mother plant. The analysis revealed amplification of BR-1 in the mutant compared to the mother stock DNA. The present inventor, without limiting himself by any theory, believes that retro-transposable elements are at least in part responsible for the occurrence of the LNL mutant.

Preferred clones of the invention are clones of Jaffa and Gal types. Jaffa clones are usually from 3.5 to 4 meters high, show a thick (relatively, e.g., to Williams clones) pseudo-stem and fingers about 22 cm (less curved than "Williams" or "GN"), have greater average bunch weight, and the bunch shape of Jaffa clones is distinctively "open". Gal clones are usually about 2.5 to 3 meters high, their fingers are 20 to 22 cm (less curved than "GN"), and their bunch shape is cylindrical and "open".

The invention will be further described and illustrated in the following example.

EXAMPLE

Initial Evaluation

The initial selection was performed on 300 mats of 'Grande Naine' produced from six mother clones, propagated by meristem culture. The in vitro cultures were initiated from apical meristem explants and were propagated and rooted as described [Cronauer S. S. et al.: Annals of Botany 53 (1984) 321-8]. Hardening, potting and growth prior to transfer to the field were carried out as practiced commercially by Rahan Meristem. After three months of ex vitro hardening, the plants were planted in the Western Galilee Banana Experimental Station. Mats were arranged in wide "tram-line" paired rows [Robinson J. C.: In: Gowens (ed). Bananas and plantains. Chapman & Hall. 1995. pp 35-36]. The distance between each pair was 6.0 m and between rows within the pair 3.0 m. The planting distances within the row were 2.7 m. Thus, the total density was 832 mats/ha. Drip irrigation, fertilization and all other agrotechnical procedures were performed according to standard methods practiced in the Western Galilee.

The evaluation was based on data collected from each individual mat over a six year period. The criterion for selection was yield per mat, calculated by adding the weight of the bunches produced in the mat. Four clones, 5/1, 6/6, 37/5 and 42/5, which performed exceptionally well, were selected for further evaluation. A fifth clone, 17/1, was selected separately in response to cold resistance characteristics (data not shown).

Out of said 300 mats that were planted, five clones performed substantially better than the control (combined value of all the clones used for the selection). The yield of each of the selected clones exceeded the control (Table 1).

Five selections 5/1, 6/6, 37/5, 42/5 and 17/1 generated 35-75% more bunches per mat compared to the average (control). The average bunch weight of all five selections exceeded the control by 2.9-7.3 kg (9.5-24%). As a consequence, the yield of the four selections was approximately twice as high as the control, while the yield of selection 17/1 was only 50% higher (Table 1).

TABLE 1

Average yield of 5 selected clones in the 6 years of the experiment, as compared to control. Yield calculated according to a density of 832 mats/ha.

| Parameter | Clone | | | | | |
|---|---|---|---|---|---|---|
| | 6/6 | 5/1 | 17/1 | 42/5 | 37/5 | Control |
| Bunch wt. (kg) | 37.47 | 37.82 | 33.44 | 37.44 | 35.68 | 30.47 |
| Bunches/mat/year | 2.83 | 2.83 | 2.33 | 2.83 | 3.00 | 1.74 |
| Calculated yield (t/ha/yr) | 87.38 | 88.19 | 64.22 | 87.31 | 88.10 | 43.59 |

Clonal Evaluation

Based on the results of the above experiment, the best clones were multiplied by meristem culture as mentioned above. Seventy plants of each of the selected clones and of a control representing the average value for all 300 original mats were used for the experiment. The planting material consisted of hardened micropropagated plants, three months after hardening. Planting distances were as mentioned above (823 mats/hectare). The plants were arranged in randomized blocks of five replicates. The numbers of bunches/mat and bunch weights were recorded for 10 mats in each replicate (excluding the mats at the end of the rows). Altogether 20-30 bunches per replicate and over 120 bunches per clone were evaluated each year. The temperatures were unusually low in the winter that followed planting, which hindered the plant growth for two consecutive cycles. The yield in the first two years was unusually low, and as a consequence the results of these cycles were ignored. The data presented here include the results of the third and fourth years after planting.

Approximately 30 hectares of micropropagated plants of the selected clones were planted in a commercial banana plantation in the Western Galilee region. These 30 hectares served as a source of explants for the evaluation experiments in the Philippines. The parameters for choosing the explants within the plant population were flowering time and yield.

In the Philippines, the performance of the selected Israeli clones was compared to the leading 'Grande Naine' selection, which was introduced to the Philippines from Ecuador. The local plants were also propagated by meristem culture and potted as mentioned above. Planting scheme in the Philippines was in "hedgerows" 4.5 m apart [Robinson J. C.: In: Gowens (ed). Bananas and plantains. Chapman & Hall. 1995. pp 35-36]. The plants were arranged within the row in a triangular configuration at distances of 1.25 m. Total density was 1973 plants per hectare. The plants were drip irrigated and fertilized according to standard methods practiced in the Philippines. The experiment was conducted in 3 separate farms, each containing both Israeli and Ecuadorian selections at a ratio of 1:1, on 50 hectares plots. The values presented are the calculated means of all three plots.

Evaluation of Selected Clones Under Israeli Conditions

Figure 1B:
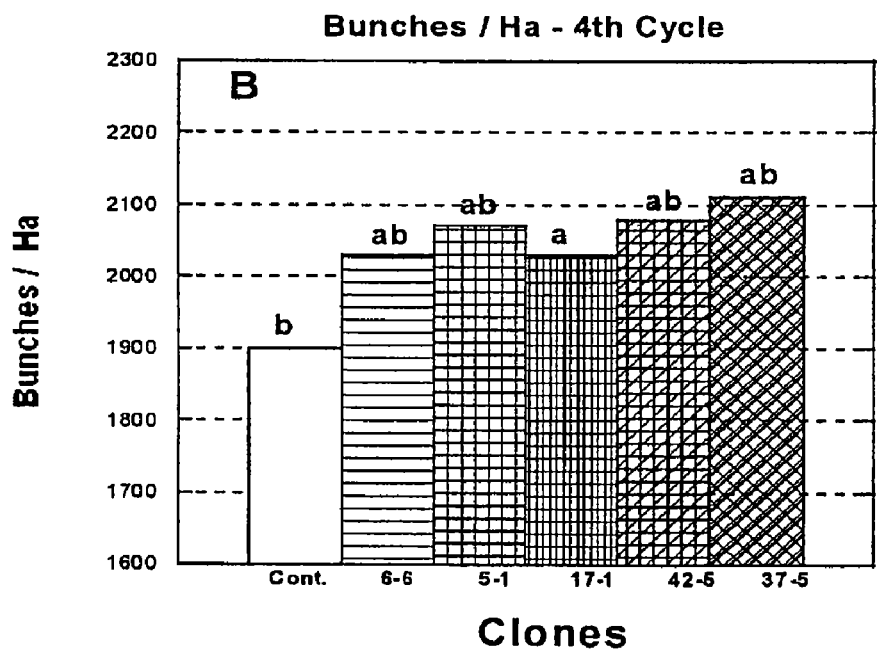
Figure 2A:
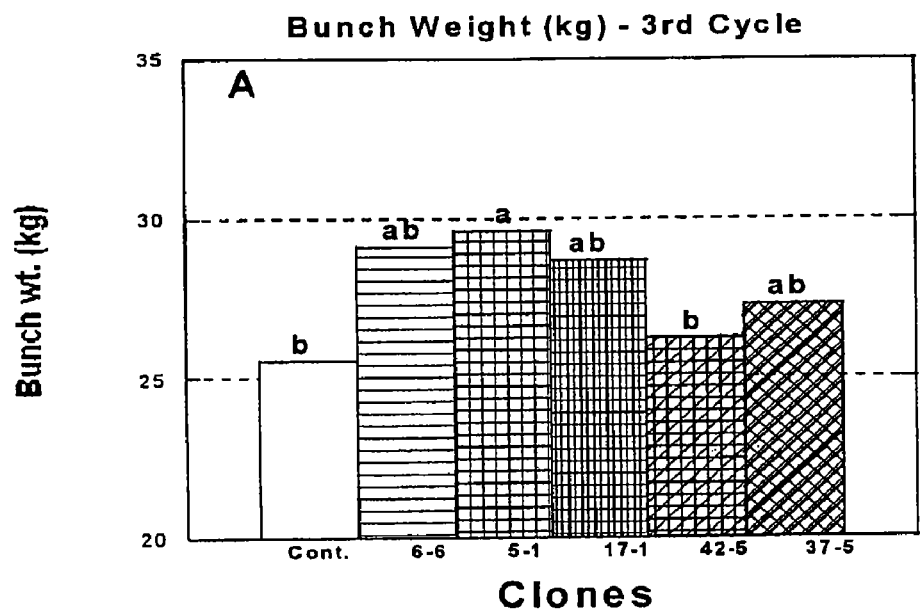
FIGS. 2A and 2B are graphs showing bunch weight of fruits harvested from selected clones.
Figure 2B:
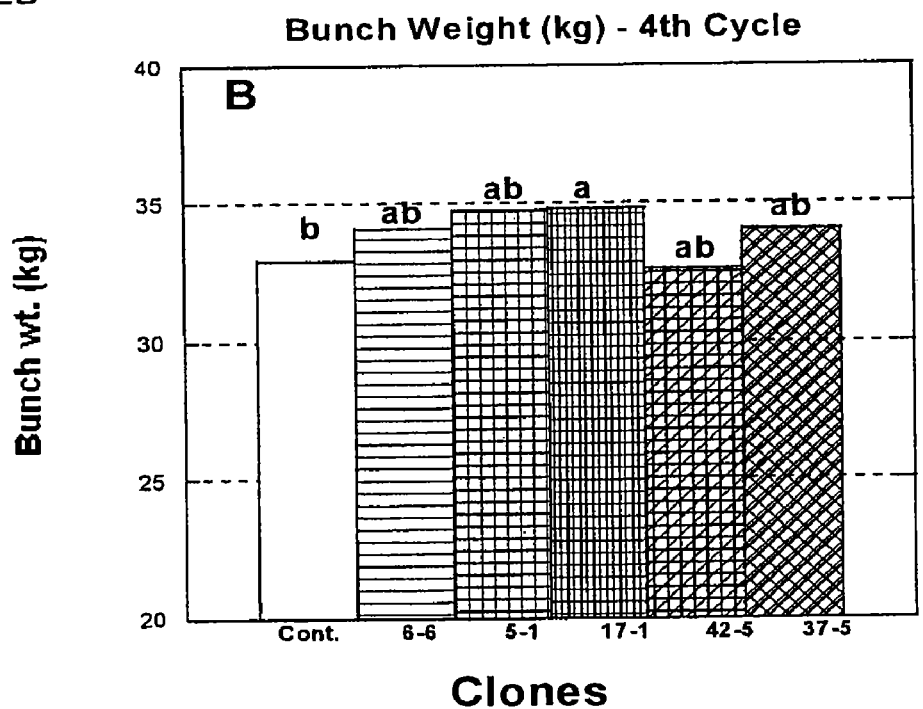

The total number of bunches/ha (FIG. 1a) of clone 17/1, 42/5, and 37/5 in the third year of production exceeded the control (42/5 not statistically significant), while clones 6/6 and 5/1 were below or similar to the control. In the fourth cycle (FIG. 1b), all the selections performed better than the control, though only in clone 17/1 the difference in the number of bunches was statistically significant (P=0.05). Clone 6/6 generated the lowest number of bunches in the third cycle (1742 compared to 1753 in the control), but at the fourth cycle it out-performed the control by approximately 10%. Selection 37/5 generated the highest number of bunches per hectare in both growth cycles (more than 11% higher than the control). Average bunch weights of selections 5/1 and 17/1 were significantly (P=0.05) above the control value in both the third and fourth cycles (FIGS. 2a and 2b). On the other hand, clone 42/5 generated the least weight per bunch in both cycles.

Figure 3A:
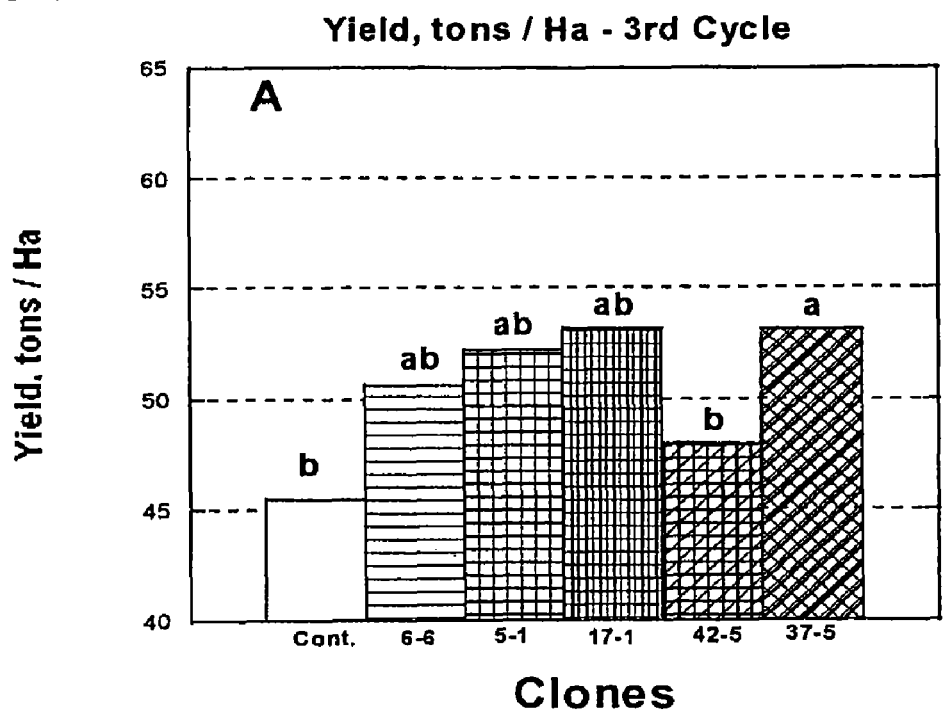
FIGS. 3A and 3B are graphs showing yields in tons per hectare of selected clones.
Figure 3B:
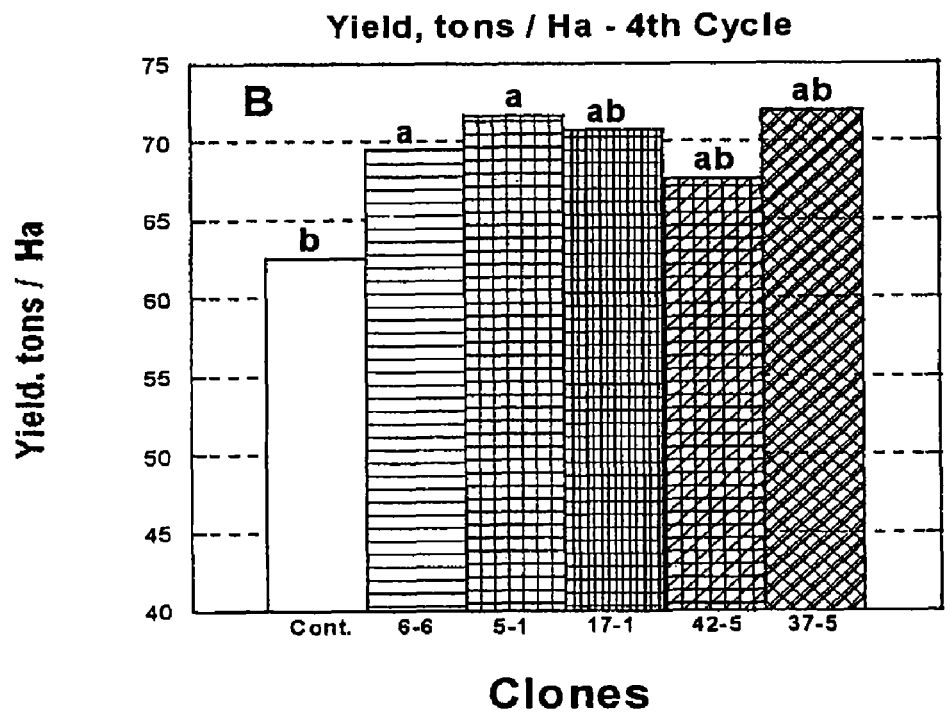

The total calculated yield, derived from the number of bunches and bunch weight, was higher in each of the clones compared to the control. The ratio between the selections followed a similar pattern (FIG. 3).

The difference in performance between the third and fourth cycle can be attributed to the difference in climatic conditions. During the winter season that preceded the third cycle, the temperatures measured in the Western Galilee were unusually low. The residual effects of the harsh climate resulted in lower yields than expected for all clones including the control. However, even under the sub-optimal conditions of the third cycle, clones 17/1 and 37/5 produced approximately 17 percent more fruit per hectare compared to the control population (FIG. 3a). The traits that mainly contribute to yield are bunch weight and the number of bunches per hectare. Our data reveal a significant difference between the clones, in the context of these two parameters. While bunches of clones 6/6 and 5/1 weighed more than 42/5, the number of bunches per hectare for 42/5 out-performed the others in both the third and fourth cycle of growth (FIGS. 1 and 3).

Comparison of Israeli Selected Clones with a Local Selection in the Philippines

Although the values for bunch weight and box/stem ratio (FIGS. 4 and 5) for Israeli selections were consistently higher throughout the 20 months of the experimental period, all selections followed a similar pattern of temporal changes in fruit production. Bunch weight of both selections gradually rose from January 1995 and reached maxima in October (FIG. 4). The weight fell during 1996 in both selections. A wide and significant difference in favor of the Israeli selection appeared from April 1995 and on. The difference reached a peak of over 30% (8.5 kg/bunch) and moderately declined in the subsequent months to approximately 5 kg/bunch (20%). Box to stem ratio, which reflects both quality and yield, was higher for the Israeli selection compared to the local one (FIG. 5). The difference gradually increased from January to October 1995 and slowly declined until very small differences were noted in the middle of the second year of measurements. The highest value of 2.26 and 1.8 boxes/stem respectively for the Israeli and local selection was reached in October 1995.

Comparison of the Originator Line with Jaffa Clone

Characteristics of a Jaffa 1 selection and the originator line R-Williams are compared in Table 2.

TABLE 2

Comparison of a selected clone, Jaffa 1, with the originator line.

| | TABLE 2A | TABLE 2B |
|---|---|---|
| Parameter | R-Williams | R-Jaffa 1 |
| Average height to inflorescence (m) | 3.40-4.0 | 3.10-3.30 |
| Average stem width at soil level after flowering (cm) | 98 | 114 |
| Average bunch weight (kg) | 35-40 | 42-45 |

TABLE 2-continued

Comparison of a selected clone, Jaffa 1, with the originator line.

|  | TABLE 2A | TABLE 2B |
|---|---|---|
| Average finger length (cm) | 21.4 | 21.5 |
| Bunch shape | Conical | Cylindrical |
| Number of hands | 10 | 12 |
| Fruits cluster appearance | Closed hands | Open hands |

The data were collected from a commercial plantation in Kibbutz Rosh Hanikra in Israel, and represent differences between two selections at the site for the third flowering cycle in the year 2003.

TABLE 3

Comparison of a selected clone, Gal 1, with the originator line.

|  | TABLE 3A | TABLE 3B |
|---|---|---|
| Parameter | R-Williams | R-Gal 1 |
| Average height to inflorescence (m) | 3.40-4.0 | 2.40-2.60 |
| Average stem width at soil level after flowering (cm) | 98 | 101 |
| Average bunch weight (kg) | 35-40 | 35-40 |
| Average finger length (cm) | 21.4 | 23..2 |
| Bunch shape | Conical | Cylindrical |
| Average number of hands | 10 | 9.8 |
| Fruits cluster appearance | Closed hands | Open hands |

The data were collected from a commercial plantation in Kibbutz Rosh Hanikra in Israel, and represent differences between two selections at the site for the third flowering cycle in the year 2003.

Characterization of Common Somaclonal Variants in Mass Propagated Banana Plants

Somaclonal variants with both high and low sensitivity to GA were generated as a consequence of an extensive duration in tissue culture. Both 'off-types' were detectable by a relatively simple bioassay developed in this laboratory (Table 4). GA sensitivity differed significantly between the different plants. The dwarf genotype had approximately 40% shorter internodes in comparison to the normal phenotype, but showed sensitivity to GA. On the other hand the 'Extra Dwarf' phenotype was insensitive to the presence of GA in the medium.

TABLE 4

Influence of $GA_3$ on "internode" length (cm) of normal in-vitro and mutant banana Grande Naine plantlets. Plantlets were grown for 5 weeks on GA-containing or hormone-free media.

| Clone / Treatment | Normal * | Dwarf | Extra dwarf mutant |
|---|---|---|---|
| Control (hormone free) | 14.2 b | 10.8 c | 9.6 d |
| GA3 (10 mg/L) | 21.7 a | 14.9 b | 9.6 d |

* Values indicated by different letters represent statistical significance (P = 0.05) using a multiple range variant analysis.

Interestingly, the occurrence of "off-types" following extensive tissue culture is higher than expected from random cell mutation. However, most detectable 'off-types' exhibit either higher or lower sensitivity to GA (Table 4). The results obtained by the GA assay on in vitro plantlets provide evidence to the hypothesis that 'Dwarf' and 'Giant' phenotypes are related to GA sensitivity.

Characterization of 'Off-types'
Induction of Variation by Extensive Duration of Meristems in In-vitro Conditions Meristem culture was performed on a single 'Grande Naine' clone employing a standard protocol used at Rahan Meristem. The meristems were sub-cultured extensively (23 cycles) to induce somaclonal variations. The in vitro plantlets were transferred to a stage III medium containing 10 ppm of gibberellic acid (GA). Analysis of GA sensitivity was examined by measuring elongation and the distance between internodes of the in vitro plants following a four weeks culture period on the GA enriched medium [2]. Further analysis of somaclonal variation was carried out in ex-vitro conditions. Following acclimatization, the plants were planted in 5 L pots and placed in a poly-ethylene covered greenhouse for approximately 16 weeks prior to selection of 'off-types'. Candidate plants showing distinct somaclonal variations were selected and used for further analysis. Stability of the different mutations was monitored following the growth of the selected clones in a commercial plantation in Rosh Hanikra, Israel.

DNA Isolation and Southern Blot Analysis

Samples (2.5 g) of fully expanded leaf blade tissue were harvested and ground by mortar and pestle under liquid nitrogen. The samples were homogenized in 25 ml extraction buffer containing 4% (w/v) CTAB, 10 mM Tris-HCl pH 8, 1.4 M NaCl and 20 mM EDTA. The extracts were placed at 65° C. for 30 min. After cooling to room temperature an equal volume of chloroform:isoamyl alcohol (20:1) was added and after 15 min. of incubation at room temperature, the mixture was centrifuged at 5000 rpm for 5 min. The supernatant was filtered through 5 layers of cheesecloth and an equal volume of ice cold iso-propanol was added to the filtrate. Following addition of NaCl to a final concentration of 0.1 M the samples were kept at −20° C. for one hour and subsequently centrifuged for 15 min. at 11,000 rpm at 40° C. The resulting pellet was resuspended in 3 ml of 70% ethyl alcohol, the mixture was centrifuged as above, and the resulting pellet was resuspended in 0.5 ml distilled water. Aliquots of ten μg DNA were digested with EcoRI and separated on a 1.2% agarose gel, stained with ethidium bromide and blotted onto a Nytran membrane. Transfer of DNA and hybridization was performed according to [Sambrook J. et al.: Molecular Cloning, A laboratory Manual. Cold Spring Harbor N.Y., Coldspring Harbor Laboratory Press].

The membranes were probed with a 344 base pair PCR product previously isolated from banana genomic DNA using Tos-17 primers [Hirochika H. et al.: Proc.Natl. Acad. Sci. USA 93 (1996) 7783-8].

RNA Isolation and RT PCR

Five grams of young leaf tissue were ground in liquid nitrogen and homogenized with extraction buffer containing 0.2 M Tris-HCl pH 8.5, 0.33 M $LiCl_2$, 10 mM EDTA and 1% PVPP (polyvinyl polypyrrolidone). The homogenate was centrifuged for 20 min. at 7000 rpm. Following centrifugation, the supernatant was filtered through five layers of cheesecloth, and then cold ethanol was added to 10% (v/v) and 3.3 M sodium acetate to 3% (v/v). The mixture was centrifuged at 10,000 rpm for 10 min., and the supernatant was collected and extracted twice with an equal volume of phenol:chloroform and once with chloroform. The aqueous phase was precipitated overnight at −20° C. with an equal volume of isopropanol and ⅒ volume of 3.3 M sodium acetate (pH 6.1). Following centrifugation at 7,000 rpm at 4° C. for 20 min., the pellet was suspended in cold 80% ethyl alcohol, centrifuged as above and finally rinsed in absolute alcohol. The pellet was resuspended in DEPC treated distilled water to a concentration of 2 μg per μl.

The RT (reverse transcriptase) reaction mixture (total volume 25 µl) contained 0.5 µg RNA, 1 mM (each) of a nucleotide mixture, 40 pmoles of oligo T18 primer, 50 units of RNAse inhibitor, 20 units of RT enzyme (AMV—Boehringer Mannheim) and 1 µl of enzyme reaction buffer. The reaction mixture was incubated for 10 min. at 25° C., 60 min. at 37° C. and 5 min. at 95° C.

PCR was performed in a 50 µl reaction mixture containing: a 1 µl aliquot from the RT reaction, 0.4 mM (each) nucleotide mixture, Tos-1 upper and lower primers (50 pmoles each) and 2.5 units of Taq-polymerase (KlenTaq). The reaction was performed at 95° C. dissociation for 2 min. followed by 25 cycles of 30 sec. at 95° C., 60 sec. of annealing at 60° C., 1 min. of primer extension at 72° C., and finally the mixture was kept at 72° C. for additional 7 min. Following the PCR the samples were separated on a 1.2% agarose gel, stained with ethidium bromide and visualized with a UV lamp.

Detection of Retro-transposons in Banana

The high frequency of deviation from the original clone, occurring during the invitro culture, suggests that the tissue culture process promotes genomic changes. However, the mechanism of somaclonal mutations in bananas is unknown. Recent studies [Hirochika H. et al.; Pro. Natl. Acad. Sci. USA 93 (1996) 7783-8] provide evidence that extensive duration of rice cell culture activated retro-transposing elements. The structural features as well as transcriptional activation of retro-elements resembled retroviruses. Under normal conditions they remain dormant and upon activation they are transcribed, reverse transcribed to cDNA molecules and reintegrated in new loci in the genome. The DNA of the pre-cultured meristem and the mutants was analyzed by Southern hybridization using BR-1 as a probe. The probe hybridized to two fragments in the control (FIG. 8), while the LNL mutant hybridized to at least four additional fragments. The addition of bands on the Southern blot indicates propagation of the retro-elements of the LNL mutants. At this point the number of integrated copies represented per band is unclear. However, in the LNL the hybridized signal was intensified. This may indicate multiplication of retro-elements in a close proximity to the original retro-sequence. This phenomenon may explain the high frequency of a single phenotypic variation. If a gene associated with GA sensitivity resides in close proximity to the original retro-sequence and the distribution of insertions is biased to short distances, we expect a high rate of mutants involving GA sensitivity.

Figure 7:
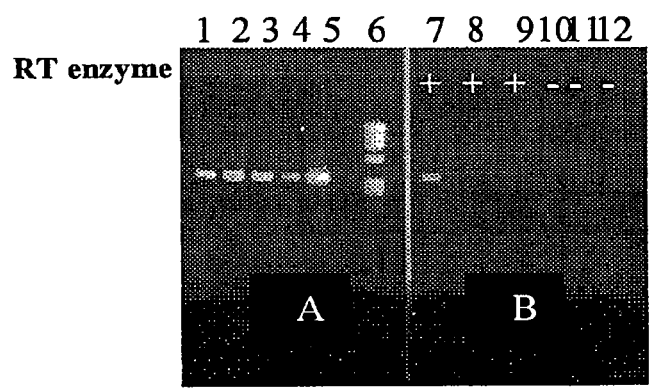
FIG. 7 is an agarose gel showing PCR products from DNA samples from LNL mutant.
Figure 8:
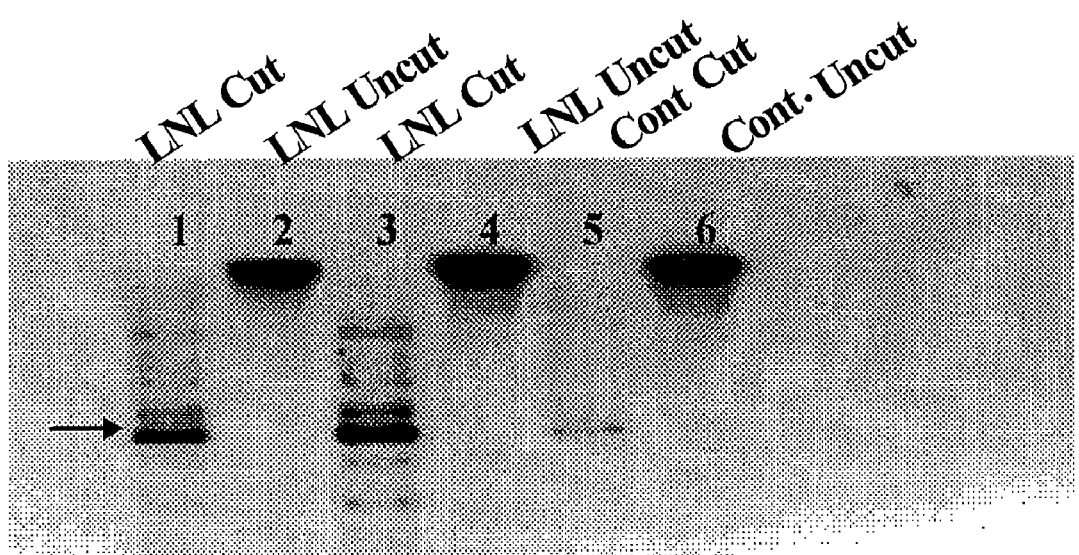
FIG. 8 is a Southern hybridization test of LNL mutants with a probe of partial retro-transposable element BR-1.

We have attempted to detect expression of retro-transposable elements in leaves from Dwarf, Extra Dwarf, and LNL plants that were induced to transcribe retro-elements by extensive duration of tissue culture. After twelve subcultures, leaf samples were analyzed for the presence of mRNA encoding retro-elements. Using a specific set of primers we were able to detect a 344 by retro-element in the LNL mutant (FIG. 7). The retro-element was only detected in the presence of the RT in the synthesis of the cDNA and was not observed in any of the six wild type plants. DNA gel blot analysis was used to estimate the complexity of retro-transposon enrichment of banana genomes following activation by tissue culture. Additional bands appeared in the lane loaded with the retro-activated mutant (LNL) DNA compared to that of the wild type (FIG. 8). Furthermore, at least two bands that were present in the control show a significant higher label intensity as compared to the wild type.

While this invention has been described in terms of some specific examples, many modifications and variations are possible. The process of the invention may be, of course, applied in geographical areas other than The Western Galilee, in which similar climatic conditions prevail. It is therefore understood that within the scope of the appended claims, the invention may be realized otherwise than as specifically described.

What is claimed is:

1. A banana clone, being Jaffa clone, said clone being a somoclonal variant of 'R-Williams", and having the characteristics as set forth in table 2 herein.

2. A banana clone, being Gal clone, said clone being a somaclonal variant of 'R-Williams", and having the characteristics as set forth in table 3 herein.

* * * * *